United States Patent [19]

Lin et al.

[11] 4,424,384

[45] Jan. 3, 1984

[54] PROCESS FOR HOMOLOGATION OF METHANOL TO ETHANOL

[75] Inventors: Jiang-Jen Lin, Round Rock; John F. Knifton, Austin, both of Tex.

[73] Assignee: Texaco Inc., White Plains, N.Y.

[21] Appl. No.: 378,531

[22] Filed: May 17, 1982

[51] Int. Cl.³ .................... C07C 29/00; C07C 31/08
[52] U.S. Cl. .................................................. 568/902
[58] Field of Search ........................................ 568/902

[56]       References Cited
        U.S. PATENT DOCUMENTS 4,205,190  5/1980  Gane et al. ..................... 568/902
4,304,946  12/1981 Isogai et al. ..................... 568/902
4,324,927  4/1982  Gauthier-Lafaye et al. ....... 568/902

Primary Examiner—J. E. Evans
Attorney, Agent, or Firm—Jack H. Park; Walter D. Hunter

[57]    ABSTRACT

Ethanol is prepared by contacting methanol, hydrogen and carbon monoxide with a catalyst system comprising an iodide-free ruthenium-containing compound, an iodide-free quaternary phosphonium or ammonium base or salt and a halide-free cobalt-containing compound, such as cobalt(III) acetylacetone or dicobalt octacarbonyl, in the presence of a substantially inert solvent.

15 Claims, No Drawings

PROCESS FOR HOMOLOGATION OF METHANOL TO ETHANOL

BACKGROUND OF THE INVENTION

1. Field of the Invention

This invention relates to an improved process for preparing ethanol from methanol by reaction with hydrogen and carbon monoxide.

2. Prior Art

A great number of processes have been described in the art for reacting methanol with carbon monoxide and hydrogen in the presence of catalyst systems to produce ethanol. A general disadvantage of the art described processes is that they all produce a wide variety of other related products such as higher molecular weight alcohols, aldehydes, hydrocarbons, carboxylic acids, esters, etc. in addition to the desired ethanol.

In U.S. Pat. Nos. 3,285,948 and 4,133,966, for example, a method of forming alcohols from methanol and synthesis gas is set out in which a cobalt catalyst system comprising cobalt carbonyl, an iodine promoter and a ruthenium halide is described. Methanol homologation to ethanol is also claimed in U.S. Pat. Nos. 4,239,924 and 4,239,925, where the catalysts comprise cobalt tricarbonyl complexes in conjunction with an iodide compound and a ruthenium compound. Riley et. al. in U.S. Pat. No. 3,248,432, and Walker in U.S. Pat. No. 4,277,634, teach the preparation of ethanol by the reaction of methanol, carbon monoxide, and hydrogen in the presence of a cobalt compound and an iodine promoter. Likewise in British Pat. No. 1,546,428 the preparation of ethanol by reacting methanol with carbon monoxide and hydrogen in the presence of a solvent such as hydrocarbon solvent, a cobalt-containing catalyst such as cobalt iodide or bromide and a tertiary phosphine. Slinkard in U.S. Pat. No. 4,168,391 teaches a process for preparing ethanol by reaction of carbon monoxide, hydrogen and methanol in the presence of cobalt carbonyl and an oxygenated solvent such as dioxane.

All of the processes described above suffer from one or more disadvantages. In many cases the conversion of methanol is low, decomposition of the catalyst to insoluble and inactive species is observed and a wide variety of products in addition to the desired ethanol are formed with consequent separation and disposal problems. There is a major disadvantage when iodine is used as part of the various catalyst systems. Iodine is very corrosive and, when used in industrial processes, is very difficult to dispose of. The catalyst which is the object of this invention comprises a ruthenium compound, a quaternary phosphonium or ammonium base or salt and a cobalt compound in a commercially attractive iodide-free system.

SUMMARY OF THE INVENTION

In the process of this invention ethanol is prepared in high yield by reacting methanol with a mixture of hydrogen and carbon monoxide. More particularly, this invention relates to a process for preparing ethanol by contacting methanol, hydrogen and carbon monoxide with a catalyst system comprising an iodide-free ruthenium-containing compound, an iodide free quaternary phosphonium or ammonium base or salt and a halide-free cobalt compound, such as cobalt(III) acetylacetonate, in the presence of a substantially inert solvent at an elevated temperature and pressure.

Recovery of ethanol from the reaction product can be carried out in any conventional or convenient manner such as by distillation, extraction, etc.

DETAILED DESCRIPTION OF THE INVENTION

The catalyst system suitable for the practice of this invention comprises an iodide-free ruthenium-containing compound, an iodide-free quaternary phosphonium base or salt and a halide-free cobalt compound as exemplified by cobalt(III) acetylacetonate or dicobalt octacarbonyl. These catalyst systems give substantially higher yields of ethanol than can be obtained when the catalyst utilized is solely a ruthenium compound together with the quaternary base or salt. Likewise, when the catalyst system employed comprises, for example, only a halide-free cobalt compound and an iodide-free quaternary phosphonium or ammonium base or salt, such as tetrabutylphosphonium bromide, no ethanol is formed.

A higher degree of conversion of methanol to the desired ethanol is achieved with the above-described catalyst combination. Also, the stability of this catalyst system is such that it can be conveniently recovered from the reaction mixture and recycled to the process.

Generally, with regard to the metallic components of the catalyst system it will contain from about 15 to about 80 mole percent of the ruthenium compound with the balance being halide-free cobalt compound based on the total number of moles of the ruthenium compound and the total number of moles of the cobalt compound in the system. Preferably, the catalyst system will contain about equimolar amounts of the ruthenium and cobalt compounds.

The iodide-free ruthenium compounds useful in this invention include any of the ruthenium oxides, such as, for example, ruthenium(IV) dioxide hydrate, anhydrous ruthenium(IV) dioxide and ruthenium(VIII) tetraoxide. Especially preferred is the use of ruthenium(IV) dioxide.

Alternatively, ruthenium may be added as the salt of certain mineral acids, as in the case of ruthenium(III) chloride hydrate, ruthenium(III) bromide, anhydrous ruthenium(III) chloride and ruthenium nitrate, or as the salt of a suitable organic carboxylic acid, for example ruthenium(III) acetate, ruthenium(III) propionate, ruthenium butyrate, ruthenium(III) trifluoroacetate, ruthenium octanoate, ruthenium napththenate, ruthenium valerate and ruthenium(III) acetylacetonate. The ruthenium may also be added to the reaction zone as a carbonyl or hydrocarbonyl derivative. Here, suitable examples include triruthenium dodecacarbonyl, hydrocarbonyls, such as $H_2Ru_4(CO)_{13}$ and $H_4Ru_4(CO)_{12}$ and substituted carbonyl species such as the tricarbonyl ruthenium(II) chloride dimer $[Ru(CO)_3Cl_2]_2$.

A wide variety of halide-free cobalt compounds are useful in the catalyst system of this invention. These halide-free containing compounds may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise cobalt in complex combination with carbon monoxide and hydrogen.

The halide-free cobalt-containing catalyst precursors may take many different forms. For instance, the cobalt may be added to the reaction mixture in an oxide form, as in the case of, for example, cobalt(II) oxide, (CoO) or cobalt(II,III) oxide ($Co_3O_4$). Alternatively, it may be added as the salt of a halide-free mineral acid, as in the case of cobalt(II) nitrate hydrate ($Co(NO_3)_2 \cdot 6H_2O$) cobalt(II) phosphate, cobalt(II) sulfate etc., or as the salt of a suitable organic carboxylic acid, for example, cobalt(II) formate, cobalt(II) acetate, cobalt(II) propionate, cobalt naphthenate, cobalt acetylacetonate, etc. The cobalt may also be added to the reaction zone as a halide-free carbonyl or hydrocarbonyl derivative. Here, suitable examples include dicobalt octacarbonyl, ($Co_2(CO)_8$), cobalt hydrocarbonyl, ($HCo(CO)_4$) and substituted carbonyl species such as the triphenylphosphine cobalt tricarbonyl dimer, etc.

Preferred cobalt-containing compounds include oxides of cobalt, cobalt salts of a halide-free mineral acid, cobalt salts of organic carboxylic acids and cobalt carbonyl or hydrocarbonyl derivatives. Among these, particularly preferred are cobalt acetylacetonate, cobalt(II) acetate, cobalt(II) propionate, and dicobalt octacarbonyl.

Quaternary phosphonium salts suitable for use in this process have the formula:

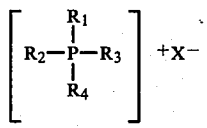

where $R_1$, $R_2$, $R_3$, and $R_4$ are organic radicals, particularly alkyl, aryl or alkaryl radicals bonded to the phosphorous atom, and X is an anionic species other than iodide. The organic radicals useful in this instance include those alkyl radicals having 1 to 20 carbon atoms in a branched or linear alkyl chain; they include, for example, the methyl, ethyl, n-butyl, iso-butyl, octyl, 2-ethylhexyl and dodecyl radicals. Tetraoctylphosphonium bromide and tetrabutylphosphonium bromide are typical examples presently in commerical production. The corresponding quaternary phosphonium and ammonium acetate, hydroxides, chlorides, nitrates, chromates and tetrafluoroborates are also satisfactory in this instance. Also useful are the corresponding quaternary ammonium bases and salts of the above series of compounds.

Equally useful are the iodide-free phosphonium and ammonium salts containing phosphorus or nitrogen bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable iodide-free quaternary phosphonium and ammonium bases and salts include tetrabutylphosphonium bromide, tetraoctylphosphonium bromide, heptyltriphenylphosphonium bromide, tetrabutylphosphonium chloride, tetrabutylphosphonium nitrate, tetrabutylphosphonium hydroxide, (n-butyl)triphenylphosphonium bromide, (n-dodecyl)triphenylphosphonium bromide, tetrabutylphosphonium tetrafluoroborate, tetrabutylphosphonium acetate, tetrabutylammonium bromide and tetramethylammonium bromide and trimethyldodecylammonium bromide.

The preferred iodide-free quaternary salts are generally the tetraalkylphosphonium or alkyl-triaryl phosphonium salts containing alkyl groups having 3–8 carbon atoms, such as butyl, hexyl and octyl and where the aryl group is phenyl. Iodide-free tetrabutylphosphonium salts, such as tetrabutylphosphonium bromide, constitute a preferred group of tetraalkylphosphonium salts for the practice of this invention.

Preferred iodide-free tetrabutylphosphonium salts or bases include the bromide, chloride, acetate salts and hydroxide base. Preferred iodide-free alkyl-triaryl phosphonium salts include, for example, heptyltriphenylphosphonium bromide, butyltriphenylphosphonium bromide, and methyltriphenylphosphonium bromide as well as the corresponding chlorides.

Generally, in the catalyst system the molar ratio of the ruthenium compound to the quaternary phosphonium or ammonium salt or base will range from about 1:0.01 to about 1:100 or more, and preferably, will be from about 1:0.5 to about 1:20.

The quantity of ruthenium compound employed in the instant invention is not critical and may vary over a wide range. In general, the novel process is desirably conducted in the presence of a catalytically effective quantity of the active ruthenium species and of the cobalt compound which gives the desired product in reasonable yield. The reaction proceeds when employing as little as about $1 \times 10^{-6}$ weight percent, and even lesser amounts, of ruthenium together with about $1 \times 10^{-6}$ weight percent or less of cobalt, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a cobalt concentration of from about $1 \times 10^{-5}$ to about 5 weight percent, based on the total weight of reaction mixture is generally desirable in the practice of this invention.

A wide variety of substantially inert solvents are useful in the process of this invention including hydrocarbon and oxygenated hydrocarbon solvents. Suitable oxygenated hydrocarbon solvents are compounds composed only of carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions, it must be relatively non-polar and it must be one which has a normal boiling point of at least 65° C. at atmospheric pressure, and preferably, the solvent will have a boiling point greater than that of ethanol and other oxygen-containing reaction products so that recovery of the solvent by distillation is facilitated.

Preferred ester type solvents are the aliphatic and acylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acylic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such a 1,4-dioxane or p-dioxane, etc. Hydrocarbon solvents, such as hexane, heptane, decane, dodecane, tetradecane, etc. are also suitable solvents for use in this invention.

In the practice of this invention, it is also possible to add a small amount of water to the solvent and still obtain satisfactory results.

The temperature range which can usefully be employed in these syntheses is a variable dependent upon other experimental factors, including the pressure, and the concentration and choice of a particular species of ruthenium catalyst, cobalt catalyst and quaternary compound utilized among other things. The range of operability is from about 150° to about 350° C. when superatmospheric pressures of syngas are employed. A narrow range of about 180°–250° C. represents the preferred temperature range.

Superatmospheric pressures of 500 psig or greater lead to substantial yields of ethanol by the process of this invention. A preferred operating range is from about 2000 psig to about 10,000 psig, although pressures above 10,000 psig also provide useful yields of ethanol.

The relative amounts of carbon monoxide and hydrogen which may be initially present in the syngas mixture can be varied widely. In general, the mole ratio of CO to $H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Higher alcohols and carboxylic acid esters may also be formed while carrying out the process of this invention. Most often these derivatives are n-propanol, methyl formate, methyl acetate, ethyl acetate, ethyl ether, etc. The major by-products of the process such as the higher molecular weight alcohols and carboxylic acid esters, are, of course, also useful compounds and major articles of commerce. The higher alcohols, the carboxylic acid esters and ethers can easily be separated from one another by conventional means, e.g., fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the ethanol product, and after recovery of the alcohol and other products, a fraction rich in ruthenium and cobalt catalyst components may then be recycled to the reaction zone, if desired, and additional products generated.

The products have been identified in this work by one or more of the following analytical procedures, viz, gas-liquid phase chromatograph (GLC), infrared (IR), mass spectrometry, nuclear magnetic resonance (nmr) and elemental analyses, or a combination of these techniques. Analyses have, for the most part, been by parts in weight; all temperatures are in degrees centigrade and all pressure in pounds per square inch gauge (psig).

The mole % selectivities to ethanol, as well as other major products of these syntheses, particularly n-propanol, methyl formate and methyl acetate, have been estimated in this work using the formula:

$$\frac{W_x/M_x}{\Sigma W_x/M_x} \times 100\%$$

Where:
X = The product of interest, e.g. ethanol, propanol, methyl formate, acetic acid, methyl acetate, ethyl acetate or n-propyl acetate.
M = The molecular weight of the product X.
$W_x$ = The concentration of the product X in the crude liquid product, as determined by GLC. The mole % conversion of methanol in these syntheses has been estimated using the formula:

$$100\% - \left[ \frac{W_{CH_3OH}/32}{\Sigma (W_x/M_x) f_x} \right] \times 100\%$$

Where:
X, M and $W_x$ are as specified above.
$f_x$ = The reaction factor for the synthesis of a particular product, i.e., the factor is 2 for the formation of MeOAc, EtOAc, n-PrOAc, but 1 for EtOH, n-PrOH, and MeOH.

Various embodiments of the process of this invention are illustrated in the following examples which are to be considered not limitative.

EXAMPLE I

A glass reactor liner was charged with 0.080 g (0.5 mmoles) of ruthenium(IV) dioxide hydrate, 1.70 g (5 mmoles) of tetra-n-butylphosphonium bromide, 0.34 g (1.0 mmoles) of dicobalt octacarbonyl, 8 g of methanol and 24 g of p-dioxane. The glass liner was placed in a stainless steel reactor. The reactor was purged of air and pressured to 1000 psi with a mixture of carbon monoxide and hydrogen (1:2 molar) and then was heated to 200° C., while it was agitated by rocking. The pressure was brought up to 4100 psi and maintained between 4100 and 3630 psig over an 18 hour period by incremental additions of the 1:2 molar mixture of carbon monoxide and hydrogen from a surge tank.

After the reactor had cooled to room temperature, an off-gas sample was taken. Excess gas was vented from the reactor following which 36.1 g of a reddish-brown product was recovered. These were no residual solids at this stage.

The liquid product was analyzed by GLC, the carbon selectivities to ethanol, n-propanol, methyl formate and methyl acetate products (basis methanol converted) were then estimated to be as follows:

76 mole % ethanol
4 mole % n-propanol
11 mole % methyl formate
2 mole % methyl acetate The methanol conversion was calculated to be 45 mole percent. The water content in the crude liquid product, as determined by Karl Fischer titration, was 5.15 wt. percent.

A typical off-gas sample showed the presence of:
54.8% hydrogen
29.0% carbon monoxide
8.4% carbon dioxide
0.6% ethane

EXAMPLE II

Following the procedures of Example I, a portion of the liquid product obtained from Example I (28.5 g) was fractionally distilled at atmospheric pressure, distillate fractions having b.p. ranges of ca. 60°–100° C. were collected, and the residual catalyst recovered as a deep-brown colored liquid (ca. 4.5 g). This residual catalyst liquid, plus methanol (8.0 g) and p-dioxane (24.0 g) were then each recharged to the glass-lined reactor of Example I. The reactor was sealed, flushed with $CO/H_2$, pressured to 5960 psi with $CO/H_2$ (1:2) and heated to 200° C. with agitation. The pressure was brought up to 5960–5735 psig by incremental additions of the carbon monoxide-hydrogen mixture and maintained for 18 hours at 200° C. In this manner the synthesis of ethanol was repeated successfully, and the latter recovered from the crude liquid product by simple distillation.

The residual catalyst solution (ca. 5.0 g) from this second cycle was again returned to the reactor for further ethanol synthesis. The syngas pressures of 3000 psi and 5775–5440 psi were used for the third and fourth cycles respectively. The methanol conversion and ethanol selectivity (mole %) for this four cycle experiment are shown in Table I below:

TABLE I
SYNTHESIS OF ETHANOL FROM METHANOL AND SYNGAS CATALYST RECYCLING

| EX-AMPLE | NUMBER OF CATALYST CYCLES | METHANOL CONVERSION (MOLE %) | ETHANOL SELECTIVITY (MOLE %) |
|---|---|---|---|
| I | 1 | 45 | 76 |
| II | 2 | 66 | 84 |
|  | 3 | 18 | 80 |
|  | 4 | 61 | 83 |

It may be noted that the selectivity to ethanol is maintained at 80 mole % in this multirecycle experiment using the iodide-free ruthenium-cobalt contained system of Example I.

EXAMPLE III

In this comparative example the experimental procedure of Example I was followed but NO cobalt-containing component was included in the catalyst. The glass-lined reactor of Example I was charged with 0.10 g (0.5 mmole) of ruthenium (IV) oxide, hydrate, 1.70 g (5.0 mmole) of tetra-n-butylphosphonium bromide, 8.0 ml methanol and 20.0 ml of p-dioxane. The reactor was pressured to 2000 psi with $CO/H_2$ (1:2), heated to 200° C. and the pressure raised to 6400 psi with $CO/H_2$ from a large surge tank. Temperature and pressure conditions were maintained for 18 hours. The reactor was then cooled, excess gas released and the reddish-brown liquid product (28.9 g) recovered.

Analysis of the liquid product showed a selectivity to ethanol of 23 mole %. The methanol conversion level was 18 mole %.

It may be noted that both the level of methanol conversion, and the selectivity to ethanol, are substantially lower in this example-without the cobalt containing compounds-than in Example I which discloses the use of a bimetallic ruthenium-cobalt catalyst system. The experiment serves then to demonstrate the importance of the cobalt-containing component in the catalyst system of Example I.

EXAMPLE IV

In this comparative example the experimental procedure of Example 1 was followed except NO ruthenium catalyst compound was included. The reactor was charged with 0.34 g (1.0 mmole) of dicobalt octacarbonyl, 3.4 g (10.0 mmoles) of tetra-n-butylphosphonium bromide, 10 ml of methanol and 10 ml of p-dioxane. After pressuring to 1000 psi with a mixture of carbon monoxide and hydrogen (1:1 molar), the reactor was heated to 200° C. while it was agitated by rocking. The pressure was brought up to 4000 psi and was maintained between 4000 and 3725 by repressuring from a surge tank. After 18 hours, the reactor was cooled rapidly, excess gas was removed by depressuring and a reddish-brown liquid product (22.7 g) recovered from the glass reactor liner.

The liquid product was analyzed by GLC. No ethanol was detected and the level of methanol conversion was 25 mole percent. This experiment serves then to demonstrate the importance of the ruthenium-containing component in the bimetallic ruthenium-cobalt catalyst system of Example I.

EXAMPLE V

In this comparative example the experimental procedures of Examples I and II were followed but NO ruthenium-containing compound and NO quaternary phosphonium salt were included in the catalyst system. The reactor was charged with 0.34 g (110 mmole) of dicobalt octacarbonyl, 8.0 g of methanol and 24.0 g of p-dioxane.

After pressuring to 1000 psi with a mixture of carbon monoxide and hydrogen (1:2 molar ratio), the reactor was heated to 200° C. while it was agitated by rocking. The pressure was brought up to 6000 psi and was maintained between 6000 and 3300 psi. After 18 hours, the reactor was cooled, excess gas was vented. The resulting material (38.4 g) appeared to be a light yellow liquid with some black solid precipitate on the bottom of the glass liner. The cobalt analysis (by atomic absorption) of the liquid product showed only 524 ppm (theoretical: 3650 ppm). Analysis of liquid product by GLC showed the following product composition: 69 mole % ethanol, 16 mole % n-propanol and 4 mole % methyl acetate the methanol conversion was calculated to be 72 mole %.

The liquid product obtained in this example was then fractionally distilled, as described in Example II, and the residual cobalt contained (4.3 g) recycled to the reactor with fresh methanol (8.0 g) and p-dioxane (24.0 g). Homologation was conducted as described above. Analysis of the liquid product (35.9 g) by GLC showed only 39 mole % ethanol, 4 mole % n-propanol, 15 mole % ethyl acetate, 3 mole % methyl acetate, and 13 mole % methyl formate. Methanol conversion was only 29 mole %.

It may be seen that the cobalt-containing catalyst alone-in the absence of the ruthenium and quaternary salt components-does not remain as active for ethanol synthesis during a typical multicycle catalyst experiment as in Example II. The experiment serves to demonstrate the importance of the ruthenium-containing component and the quaternary salt component in the catalyst system of Examples I and II.

EXAMPLE VI

Following the procedures of Example I, the glass-lined reactor was charged with 0.19 g (1.0 mmole) of ruthenium(IV) dioxide hydrate, 3.4 g (10 mmoles) of tetra-n-butylphosphonium bromide, 0.34 g (1.0 mmoles) of dicobalt octacarbonyl, 10 ml of methanol and 25 ml of p-dioxane. The glass liner was placed in a stainless steel reactor. The reactor was purged of air and pressured to 1000 psi with a mixture of carbon monoxide and hydrogen (1:1 molar) and then was heated to 200° C., while it was agitated by rocking. The pressure was brought up to 4075 psig and maintained between 4075 and 3285 psig over an 18 hour period by incremental addition of the 1:1 molar ratio mixture of carbon monoxide and hydrogen from a surge tank.

After the reactor had cooled to room temperature, excess gas was vented and the reddish-brown liquid product (36.9 g) was recovered.

The liquid product was analyzed by GLC, the carbon selectivities to ethanol, n-propanol, methyl formate and methyl acetate products were then estimated as follows:
66.0 mole % ethanol
6.0 mole % n-propanol
2.0 mole % methyl formate
17.0 mole % methyl acetate
6.0 mole % ethyl acetate The methanol conversion was calculated to be 57 mole percent.

The product liquid was also analyzed for cobalt content by atomic absorption. The cobalt content (3214 ppm) represents 99% cobalt recovery in solution using the ruthenium-cobalt catalyst of this invention.

EXAMPLE VII

Following the general procedure of Example I a reactor was charged with 0.05 g (0.25 mmoles) of ruthenium(IV) dioxide hydrate, 0.84 g (2.5 mmoles) of tetra-n-butylphosphonium bromide, 0.34 g (1.0 mmoles) of dicobalt octacarbonyl 10 ml of methanol and 20 ml of n-heptane. After placing the liner in a stainless steel reactor the reactor was purged of air and pressured to 1000 psi with a mixture of carbon monoxide and hydrogen (1:2 molar) and then was heated to 200° C., while it was agitated by rocking. The pressure was brought up to 4500 psig and held constant over an 18 hour period.

At the end of this period, the reactor was cooled to room temperature, and an off-gas sample was taken. Excess gas was vented from the reactor following which 21.3 g of a reddish-brown product was recovered.

The liquid product was analyzed by GLC, the carbon selectivities to ethanol, n-propanol and methyl formate products were estimated to be as follows:
73.0 mole % ethanol
7.0 mole % n-propanol
8.0 mole % methyl formate The methanol conversion was calculated to be 12 mole percent.

EXAMPLE VIII

As with the previous examples, the reactor was charged with 0.19 g (1.0 mmoles) of ruthenium(IV) dioxide hydrate, 10 mmole of tetra-n-butylphosphonium bromide, 3.4 g (1.0 mmoles) of cobalt(III) acetylacetonate, 10 ml of methanol and 10 ml of p-dioxane. The reactor was purged of air and pressured to 1000 psi with a mixture of carbon monoxide and hydrogen (1:1 molar) and then was heated to 200° C., while it was agitated by rocking. The pressure was brought up to 4000 psig, and maintained between 4000 and 3110 psig over an 18 hour period by incremental addition of the 1:1 molar mixture of carbon monoxide and hydrogen from a surge tank.

After the reactor cooled to room temperature, an off-gas sample was taken. Excess gas was vented from the reactor following which 25.5 g of a reddish-brown product was recovered.

Analysis of the liquid product by GLC showed the following product composition:
60.0 mole % ethanol
9.0 mole % n-propanol
7.0 mole % methyl formate
17.0 mole % methyl acetate
2.0 mole % ethyl acetate The methanol conversion was calculated to be 42 mole percent.

EXAMPLE IX

A glass reactor liner was charged with 0.19 g (1.0 mmmoles) of ruthenium(IV) dioxide hydrate, 3.4 g (10.0 mmoles) of tetra-n-butylphosphonium bromide, 0.34 g (1.0 mmoles) of dicobalt octacarbonyl, 10 ml of methanol, 10 ml of p-dioxane and 1 ml of water. The reactor was purged of air and pressured to 1000 psi with a mixture of carbon monoxide and hydrogen (1:1 molar) and then was heated to 200° C., while it was agitated by rocking. The pressure was brought up to 4100 psi and maintained between 4100 and 3410 psig over an 18 hour period by incremental addition of the 1:1 molar mixture of carbon monoxide and hydrogen from a surge tank.

As with the other examples, the reactor was cooled, vented and the product recovered.

Excess gas was vented from the reactor following which 22.4 g of a reddish-brown product was recovered.

Analysis of the liquid product by GLC showed the following product composition:
70.0 mole % ethanol
7.0 mole % n-propanol
6.0 mole % methyl formate
12.0 mole % methyl acetate The methanol conversion was calculated to be 48 mole percent.

EXAMPLE X

The Example I was repeated, except the catalyst composition was ruthenium(III) chloride, (0.244 g, 1.0 mm) tetra-n-butylphosphonium bromide (3.4 g, 10 mm) and dicobalt octacarbonyl (0.34 g, 1 mmole), and the reaction conditions were 6400 psi, $CO/H_2$—1:2, 200° C. and 18 hours the following results were obtained:
60 mole % ethanol
12 mole % n-propanol
9 mole % methyl acetate
10 mole % ethyl acetate The conversion of methanol was calculated to be 85 mole %.

EXAMPLE XI

The Example I was repeated, except the catalyst composition was triruthenium dodecacarbonyl (0.213 g, 0.33 mmole), tetra-n-butylphosphonium bromide (3.4 g, 10 mmoles) and dicobalt octacarbonyl (0.34 g, 1 mmole) and the reacting conditions were 6000 psi CO/H$_2$—1:2.200° C. and 18 hours the following results were obtained.

68 mole % ethanol
12 mole % n-propanol
11 mole % methyl acetate
6 mole % ethyl acetate The conversion of methanol was calculated to be 66 mole %.

What is claimed is:

1. A process for preparing ethanol which comprises contacting a mixture of carbon monoxide, hydrogen, and methanol with an iodide-free catalyst system comprising a ruthenium-containing compound, an iodide-free quaternary phosphonium base or salt and a halide-free cobalt-containing compound in the presence of a substantially inert solvent at a pressure of 500 psig or greater, and at a temperature of about 150° C. or greater.

2. The process of claim 1 wherein the said ruthenium compound is selected from the group consisting of anhydrous ruthenium dioxide, ruthenium(IV) dioxide hydrate and ruthenium(VIII) tetraoxide, ruthenium(III) chloride and triruthenium dodecacarbonyl.

3. The process of claim 1 wherein the said ruthenium compound is ruthenium(IV) dioxide hydrate.

4. The process of claim 1 wherein the said iodide-free quaternary phosphonium base or salt is an iodide-free quaternary phosphonium salt.

5. The process of claim 4 wherein the said quaternary phosphonium salt is selected from the group comprising an iodide-free tetraalkylphosphonium salt and an iodide-free alkyltriarylphosphonium salt.

6. The process of claim 5 wherein the said quaternary phosphonium salt is tetra-n-butylphosphonium bromide.

7. The process of claim 1 wherein the halide-free cobalt-containing compound is selected from the group consisting of cobalt(II) oxide, cobalt(II) nitrate, cobalt sulfate, cobalt(II) acetate, cobalt propionate, cobalt(III) acetylacetonate and dicobalt octacarbonyl.

8. The process of claim 1 wherein the halide-free cobalt-containing compound in the catalyst system is dicobalt octacarbonyl.

9. The process of claim 1 wherein the halide-free cobalt-containing compound in the catalyst system is cobalt(III) acetylacetonate.

10. The process of claim 1 wherein the said substantially inert solvent is an oxygenated hydrocarbon solvent.

11. The process of claim 1 wherein the said substantially inert solvent is p-dioxane.

12. The process of claim 1 wherein the process is conducted at a pressure of about 500 to about 10,000 psig.

13. The process of claim 1 wherein the process is conducted at a pressure of about 2000 to about 10,000 psig.

14. The process of claim 1 wherein the process is conducted at a preferred temperature of about 180° to about 250° C.

15. The process of claim 1 wherein the said catalyst system comprises ruthenium(IV) dioxide, tetra-n-butylphosphonium bromide and dicobalt octacarbonyl.

* * * * *